US011253184B2

(12) United States Patent
Shute et al.

(10) Patent No.: US 11,253,184 B2
(45) Date of Patent: Feb. 22, 2022

(54) SYSTEMS AND METHODS FOR RECONSTRUCTING HEART SOUNDS

(71) Applicant: Cardiac Pacemakers, Inc., St. Paul, MN (US)

(72) Inventors: Jonathan Bennett Shute, Minnetonka, MN (US); Bin Mi, Arden Hills, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 154 days.

(21) Appl. No.: 16/519,853

(22) Filed: Jul. 23, 2019

(65) Prior Publication Data
US 2020/0077913 A1 Mar. 12, 2020

Related U.S. Application Data

(60) Provisional application No. 62/728,240, filed on Sep. 7, 2018.

(51) Int. Cl.
*A61B 5/00* (2006.01)
*A61B 5/349* (2021.01)
(Continued)

(52) U.S. Cl.
CPC ............ *A61B 5/349* (2021.01); *A61B 5/0205* (2013.01); *A61B 5/283* (2021.01); *A61B 5/6869* (2013.01);
(Continued)

(58) Field of Classification Search
CPC ..... A61B 5/0205; A61B 5/024; A61B 5/7203; A61B 7/00; A61B 7/6869
See application file for complete search history.

(56) References Cited

U.S. PATENT DOCUMENTS

2004/0106960 A1 6/2004 Siejko et al.
2004/0167417 A1* 8/2004 Schulhauser .......... A61B 7/003
600/513
(Continued)

FOREIGN PATENT DOCUMENTS

WO WO-2019055885 A1 3/2019
WO WO-2020050918 A1 3/2020

OTHER PUBLICATIONS

"International Application Serial No. PCT/US2019/043006, International Preliminary Report on Patentability dated Mar. 18, 2021", 8 pgs.

(Continued)

*Primary Examiner* — Allen Porter
(74) *Attorney, Agent, or Firm* — Schwegman Lundberg & Woessner, P.A.

(57) ABSTRACT

Systems and methods for reconstructing heart sounds from heart sound samples taken under a sub-optimal condition, such as at a low sampling rate, are discussed. An exemplary system receives acceleration information from a patient sensed at a first sampling rate, and generate a heart sound ensemble of portions of acceleration information over multiple cardiac cycles. The system can reconstruct a heart sound segment to have a second sampling rate, higher than the first sampling rate, using the generated heart sound ensemble. A heart sound metric can be generated using the reconstructed heart sound segment, and used for detecting a cardiac event, such as a cardiac arrhythmia episode, or a worsening heart failure event.

20 Claims, 7 Drawing Sheets

(51) Int. Cl.
*A61B 5/0205* (2006.01)
*A61B 5/283* (2021.01)
*A61B 7/04* (2006.01)
*A61N 1/36* (2006.01)
*A61N 1/362* (2006.01)

(52) U.S. Cl.
CPC .......... *A61B 5/0031* (2013.01); *A61B 5/7203* (2013.01); *A61B 5/7285* (2013.01); *A61B 7/04* (2013.01); *A61B 2562/0219* (2013.01); *A61N 1/362* (2013.01); *A61N 1/36014* (2013.01)

(56) References Cited

U.S. PATENT DOCUMENTS

| | | | | |
|---|---|---|---|---|
| 2006/0270939 | A1* | 11/2006 | Wariar | A61B 7/00 600/528 |
| 2007/0049974 | A1* | 3/2007 | Li | A61B 5/363 607/4 |
| 2008/0188721 | A1 | 8/2008 | Patangay et al. | |
| 2011/0066042 | A1 | 3/2011 | Pandia et al. | |
| 2013/0237873 | A1* | 9/2013 | Zhang | A61B 5/686 600/513 |
| 2015/0057512 | A1* | 2/2015 | Kapoor | A61B 5/0205 600/324 |
| 2016/0000380 | A1 | 1/2016 | Averina et al. | |
| 2017/0291022 | A1* | 10/2017 | Shuros | A61N 1/36578 |
| 2020/0245889 | A1* | 8/2020 | Telenkov | A61B 5/316 |

OTHER PUBLICATIONS

"International Application Serial No. PCT/US2019/043006, International Search Report dated Nov. 19, 2019", 5 pgs.

"International Application Serial No. PCT/US2019/043006, Written Opinion dated Nov. 19, 2019", 6 pgs.

Choudhary, Tilendra, et al., "Heart Sound Extraction From Sternal Seismocardiographic Signal", IEEE Signal Processing Letters, vol. 25, No. 4, (Apr. 1, 2018), 482-486.

* cited by examiner

US 11,253,184 B2

SYSTEMS AND METHODS FOR RECONSTRUCTING HEART SOUNDS

CLAIM OF PRIORITY

This application claims the benefit of priority under 35 U.S.C. § 119(e) of U.S. Provisional Patent Application Ser. No. 62/728,240, filed on Sep. 7, 2018, which is herein incorporated by reference in its entirety.

TECHNICAL FIELD

This document relates generally to medical systems, and more particularly, to systems, devices and methods for sensing heart sounds from a subject.

BACKGROUND

Heart sounds are associated with mechanical vibration of a heart and blood flow through the heart. Heart sounds recur with each cardiac cycle and are separated and classified according to the activity associated with the vibration. Typically, heart sounds sensed from a subject may include several components within a cardiac cycle, including a first (S1), a second (S2), a third (S3), or a fourth (S4) heart sound. S1 is associated with the vibrational sound made by the heart during tensing of the mitral valve. S2 is produced by closure of the aortic and pulmonary valves, and marks the beginning of diastole. S3 is an early diastolic sound corresponding to passive ventricular filling during diastole, when the blood rushes into the ventricles. S4 is a late diastolic sound corresponding to active ventricular filling when the atria contract and push the blood into the ventricles. In a healthy subject. S3 is usually faint and S4 is rarely audible. However, a pathologic S3 or S4 may be higher pitched and louder.

Heart sounds have been used to assess cardiac systolic and diastolic functions. Systole is the contraction or a period of contraction of the heart that causes blood to be forced out of the heart such as the ventricles and into the aorta and pulmonary artery. Diastole is the relaxation or a period of relaxation of the heart during which the blood flows back into the heart such as the ventricles. Patients with cardiac diseases may have deteriorated systolic or diastolic functions. For example, congestive heart failure (CHF) occurs when the heart is unable to supply enough blood to maintain a healthy physiologic state.

Implantable medical devices (IMDs) have been used to monitor patients with cardiac disease, such as to detect cardiac events leading to worsening heart failure (WHF). An IMD may sense physiologic signals from a patient, and deliver electrostimulation therapy to improve cardiac performance in CHF patients. Frequent patient monitoring via an IMD may help identify patients having an elevated risk of developing future heart failure events, ensure timely treatment, reduce heart failure hospitalization, improve patient outcome, and reduce healthcare cost.

OVERVIEW

An ambulatory medical device (AMD), such as an implantable medical device (IMD), a subcutaneous medical device, a wearable medical device, or other external medical device, may be used to monitor cardiac patient. An AMD may sense electrical or mechanical activities of the heart via sensing electrodes and/or physiologic sensors, and detect cardiac events such as cardiac arrhythmias, or worsening of heart failure (WHF). An IMD may include a pulse generator capable of generating and delivering electrostimulation therapy to the heart or other excitable tissue (e.g., neural targets) to restore or improve cardiac performance in a CHF patient, or to correct cardiac arrhythmia. For example, a detection of cardiac arrhythmia may trigger cardiac pacing or electric shock, or a detection of a WHF event may trigger electrostimulation therapy, such as a resynchronization therapy (CRT) to correct cardiac dyssynchrony in patients with heart failure.

An IMD can detect a cardiac event using heart sounds (HS) detected from a patient. For example, S1 and/or S2 may be used to detect cardiac arrhythmia such as supraventricular tachycardia or ventricular tachycardia. Pulmonary fluid accumulation in CHF patients may cause elevated ventricular filling pressure and diastolic dysfunction, resulting in pathologically louder S3. Forceful atrial contraction to overcome an abnormally stiff ventricle in a CHF patient may produce profound S4. Therefore, monitoring S3 or S4 may help determining patient diastolic dysfunction, detecting a WHF event, or assessing patient risk of developing future WHF.

Ambulatory heart sounds detection involves placing a heart sound sensor at an epicutaneous or a subcatenous location at or near the heart. The heart sound sensor, such as an accelerometer, may be included within an IMD for subcutaneous implantation, or associated with an implantable lead for epicardial or endocardial placement. S1 and S2 heart sounds generally have a frequency within a range of approximately 10-250 Hz, With a wide interpersonal variability and shifts secondary to technical equipment, S2 generally has a higher frequency than S1. For example, most of S1 power fall within approximately 10-50 Hz and most of S2 fall within approximately 20-70 Hz. Early diastole sound S3 produced by rapid filling of dilated ventricles, and late diastole sound S4 produced by contraction of the left atrium against a non-compliant left ventricle, when present, generally have lower intensity and lower frequencies.

High-resolution heart sounds signal sampled at high frequency have found many applications in cardiovascular diagnostics, including detection of cardiac events such as cardiac arrhythmia, WHF, or assessment of cardiac function. Under the Nyquist sampling theorem, the AMD needs to sample the HS at a sampling rate sufficiently high (e.g., approximately 200-500 Hz) to preserve certain high frequency content of a HS signal, such as S2 heart sound that spans a frequency range of approximately 50-100 Hz, among other HS metrics such as amplitude and/or timing of peaks of S1, S2, S3, or S4 heart sounds. However, data acquisition at a high sampling rate may consume a significant amount of battery power. For a battery-powered ambulatory system such as an implantable cardiac device, high battery power drain may shorten the device life. Moreover, high-rate HS data acquisition puts a higher demand for device memory to store a large volume of HS data, as well as a higher demand for communication bandwidth to transmit the HS data from the AMD to an external system for data processing and presentation. For at least these reasons, the present inventors have recognized an unmet need for ambulatory HS monitoring systems and methods for producing high-rate heart sounds data in a power-efficient and cost-effective manner.

The present document discusses systems, devices, and methods for reconstructing HS to have a desired sampling rate (or data rate) using HS samples taken under a sub-optimal condition, such as a low sampling rate. An exemplary system includes a data receiver circuit to receive physiologic information including acceleration information indicative of HS sensed at a first sampling rate. The system includes a control circuit configured to generate a HS ensemble using the received acceleration information over multiple cardiac cycles, and to reconstruct a HS segment to have a second sampling rate higher than the first sampling rate using the generated HS ensemble. The control circuit may generate a HS metric using the reconstructed HS segment. A physiologic event detector may detect a cardiac event using the generated HS metric.

Example 1 is a system for sensing heart sounds that comprises a data receiver circuit configured to receive acceleration information from a patient sensed at a first sampling rate, and a control circuit configured to generate a HS ensemble using the received acceleration information over multiple cardiac cycles, reconstruct a HS segment to have a second sampling rate different than the first sampling rate using the generated HS ensemble, and provide the reconstructed HS segment to a user or a process.

In Example 2, the subject matter of Example 1 optionally includes the second sampling rate that may be higher than the first sampling rate.

In Example 3, the subject matter of any one or more of Examples 1-2 optionally includes the reconstructed HS segment that may include one or more of an S1 segment, an S2 segment, an S3 segment, or an S4 segment within a cardiac cycle.

In Example 4, the subject matter of any one or more of Examples 1-3 optionally includes the control circuit that may be configured to reconstruct a first HS segment to have the second sampling rate, and reconstruct a second HS segment to have a third sampling rate different than the first and second sampling rates, the first and second HS segments representing different segments of a cardiac cycle.

In Example 5, the subject matter of any one or more of Examples 1-4 optionally includes the control circuit that may be configured to align the portions of the received acceleration information over multiple cardiac cycles with respect to respective fiducial points corresponding to the multiple cardiac cycles, and generate the HS ensemble using the aligned portions of the received acceleration information.

In Example 6, the subject matter of any one or more of Examples 1-5 optionally includes the control circuit that may be configured to produce reconstruction time windows each having a duration inversely proportional to the second sampling rate, and reconstruct the HS segment using HS data of the generated HS ensemble falling within the produced reconstruction time windows.

In Example 7, the subject matter of Example 6 optionally includes the control circuit that may be configured to reconstruct the HS segment using a central tendency of the HS data within each of the produced reconstruction time windows.

In Example 8, the subject matter of any one or more of Examples 1-7 optionally includes the data receiver circuit that may be configured to receive heart rates (HRs) or cycle lengths (CLs) measured concurrently with the acceleration information, and the control circuit that may be configured to generate the HS ensemble including portions of the received acceleration information over multiple cardiac cycles with corresponding received HRs or CLs falling within a specified range.

In Example 9, the subject matter of any one or more of Examples 1-8 optionally includes the data receiver circuit that may be configured to receive physical activity level sensed concurrently with the acceleration information, and the control circuit that may be configured to generate the HS ensemble including portions of the received acceleration information over multiple cardiac cycles with corresponding received physical activity level falling within a specified activity range.

In Example 10, the subject matter of any one or more of Examples 1-9 optionally includes the data receiver circuit that may be configured to receive respiratory rates sensed concurrently with the acceleration information, and the control circuit that may be configured to generate the HS ensemble including portions of the received acceleration information over multiple cardiac cycles with corresponding received respiratory rates falling within a specified respiratory rate range.

In Example 11, the subject matter of any one or more of Examples 1-10 optionally includes the data receiver circuit that may be configured to receive information about time of a day during which the acceleration information is sensed, and the control circuit that may be configured to generate the HS ensemble including portions of the received acceleration information over multiple cardiac cycles corresponding to substantially the same time of a day.

In Example 12, the subject matter of any one or more of Examples 1-11 optionally includes the data receiver circuit coupled to an accelerometer and configured to receive a body motion signal at a first sampling rate, and the control circuit may be configured to: detect one or more of a physical activity level or a respiratory rate using the sensed body motion signal; identify portions of the sensed body motion signal corresponding to the detected physical activity level falling within a specified physical activity range or the detected respiratory rate falling within a specified respiratory rate range; and generate a HS ensemble including multiple cardiac cycles of the identified portions of the sensed body motion signal.

In Example 13, the subject matter of any one or more of Examples 1-12 optionally includes the control circuit that may be configured to generate a HS metric including an intensity metric or a timing metric of one or more of a first (S1), second (S2), third (S3), or fourth (S4) heart sound component measured from the reconstructed HS segment.

In Example 14, the subject matter of Example 13 optionally includes a physiologic event detector configured to detect a cardiac event using the generated HS metric.

In Example 15, the subject matter of Example 14 optionally includes a therapy circuit configured to initiate or adjust a therapy in response to the detected cardiac event.

In Examples 16, the subject matter of any of Examples 1-15 optionally includes the HS ensemble that may include portions of acceleration information sensed at the first sampling rate. The first sampling rate may include at least one of an activity sensing sampling rate, a respiration sensing sampling rate, or a low-power sampling rate.

Example 17 is a method for sensing heart sounds. The method comprises steps of: receiving acceleration information from a patient sensed at a first sampling rate; generating a HS ensemble using the received acceleration information over multiple cardiac cycles; reconstructing a HS segment to have a second sampling rate different than the first sampling rate using the generated HS ensemble; and providing the reconstructed HS segment to a user or a process.

In Example 18, the subject matter of Example 17 optionally includes the reconstructed HS segment that may include one or more of an S1 segment, an S2 segment, an S3 segment, or an S4 segment within a cardiac cycle. The reconstruction of the HS segment may include reconstructing a first HS segment to have the second sampling rate, and reconstructing a second HS segment to have a third sampling rate different than the first and second sampling rates, the first and second HS segments representing different segments of a cardiac cycle.

In Example 19, the subject matter of any one or more of Examples 17-18 optionally includes reconstructing the HS segment that may include producing reconstruction time windows each having a duration inversely proportional to the second sampling rate, and reconstructing the HS segment using a central tendency of HS data of the generated HS ensemble falling within the produced reconstruction time windows.

In Example 20, the subject matter of any one or more of Examples 17-19 optionally includes steps of receiving one or more of physiologic parameters concurrently measured with the acceleration information, the one or more physiologic parameters including heart rates (HRs), cycle lengths (CLs), physical activity level, or respiratory rates, and generating the HS ensemble including portions of the received acceleration information over multiple cardiac cycles with corresponding received one or more physiologic parameters satisfying specified condition.

In Example 21, the subject matter of any one or more of Examples 17-20 optionally includes generating the HS ensemble including portions of the received acceleration information over multiple cardiac cycles that are sensed during substantially the same time of a day.

In Example 22, the subject matter of any one or more of Examples 17-21 optionally includes steps of: receiving a body motion signal at a first sampling rate; detecting one or more of a physical activity level or a respiratory rate using the sensed body motion signal; identifying portions of the sensed body motion signal corresponding to the detected physical activity level falling within a specified physical activity range or the detected respiratory rate falling within a specified respiratory rate range; and generating a HS ensemble including multiple cardiac cycles of the identified portions of the sensed body motion signal.

In Example 23, the subject matter of any one or more of Examples 17-22 optionally includes steps of generating a HS metric including an intensity metric or a timing metric of one or more of a first (S1), second (S2), third (S3), or fourth (S4) heart sound component measured from the reconstructed HS segment, detecting a cardiac event using the generated HS metric, and initiating or adjusting a therapy in response to the detected cardiac event.

The heart sound reconstruction discussed herein may improve the functionality of an ambulatory medical device (e.g., an implantable cardiac device capable of monitoring, among other signals, heart sounds), or a medical diagnostic system or device that uses HS to detect a physiologic event, such as a cardiac arrhythmia episode or a WHF event. Conventionally, HS monitoring typically requires a high sampling rate (e.g., around 200-500 Hz) to capture the frequency contents of certain HS components of interest, such as S2. High-rate data acquisition may consume a substantial amount of power, reduce battery life and device longevity, and take up more memory space and data communication bandwidth. To conserve power and system resources and reduce cost, less frequent HS monitoring may be necessary in conventional ambulatory devices. However, this may not be clinically feasible for those patients who need more intensive and continuous monitoring. Additionally, some ambulatory devices use the same sensor (e.g., an accelerometer) to monitor multiple physiologic parameters, such as physical activity, posture, respiration, and cardiac vibration. Some of these physiologic parameters may be reliably detected from a sensor signal sensed at a relatively much lower frequency (e.g., approximately 10-20 Hz) than the requirement for high rate and high-resolution HS. To sense various physiologic parameters with different sampling rate requirements, the sensing circuitry may operate at different sensing modes, such as alternating between a high sampling rate to provide data for HS analysis and a low sampling rate to provide data for physical activity and/or respiration analysis, or alternating between different power modes, such as alternating between a high-power mode having a high sampling rate and a low-power mode having a low sampling rate. The multiple sensing modes and frequent sampling rate switching increase the system complexity and cost.

This document describes HS reconstruction systems and devices that can reconstruct a high-frequency HS segment using multiple epochs of sensor data sampled at sub-optimal conditions, such as a lower sampling rate at 10-20 Hz. In an example, the present systems and devices can recycle low-rate sensor (e.g., accelerometer) signals acquired for physical activity and/or respiration detection. Because the low-rate sensor data acquisition consumes less power, the battery life and device longevity can be extended. For patients requiring long-term and continuous ambulatory monitoring, the effectual ambulatory HS monitoring can be extended by using the reconstructed HS segment. Recycling the low-rate sensor data may also help save storage space and communication bandwidth, and reduce the complexity and cost of the system and device for monitoring HS and using HS to guide medical diagnostic and therapy.

The HS reconstruction discussed in this document differs from, and is advantageous to, conventional approaches of reconstructing from a low-rate data source, such as data interpolation and/or extrapolation, data smoothing, or other up-sampling techniques. These conventional techniques do not use additional data samples taken from the data source. For example, the up-sampling achieves a higher data rate (or temporal resolution) algorithmically by zero stuffing between existing data samples followed by filtering. The resultant interpolated or smoothed signal, even though having a finer temporal resolution, does not recover higher frequency content from the data source. In contrast, the HS reconstruction discussed in this document achieves finer temporal resolution (i.e., higher sampling rate) using multiple epochs of HS data from the signal source. As such, the reconstructed HS segment may more reliably capture certain high-frequency signal contents embedded in various epochs of the HS signal.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for reconstructing heart sounds from HS samples taken under a sub-optimal condition, such as at a low sampling rate. An exemplary system receives acceleration information sensed from a subject at a first sampling rate, and generate a HS ensemble of portions of the acceleration information over multiple cardiac cycles. The system may use the HS ensemble to reconstruct a HS segment to have a second sampling rate higher than the first sampling rate. The reconstructed HS segment may include HS signal for a cardiac cycle or a particular HS component (e.g., S1, S2, S3, or S4). A HS metric may be generated from the reconstructed HS segment, and used to establish medical diagnostics, or to detect an arrhythmia episode, a WHF event, or other cardiac events.

Figure 1:
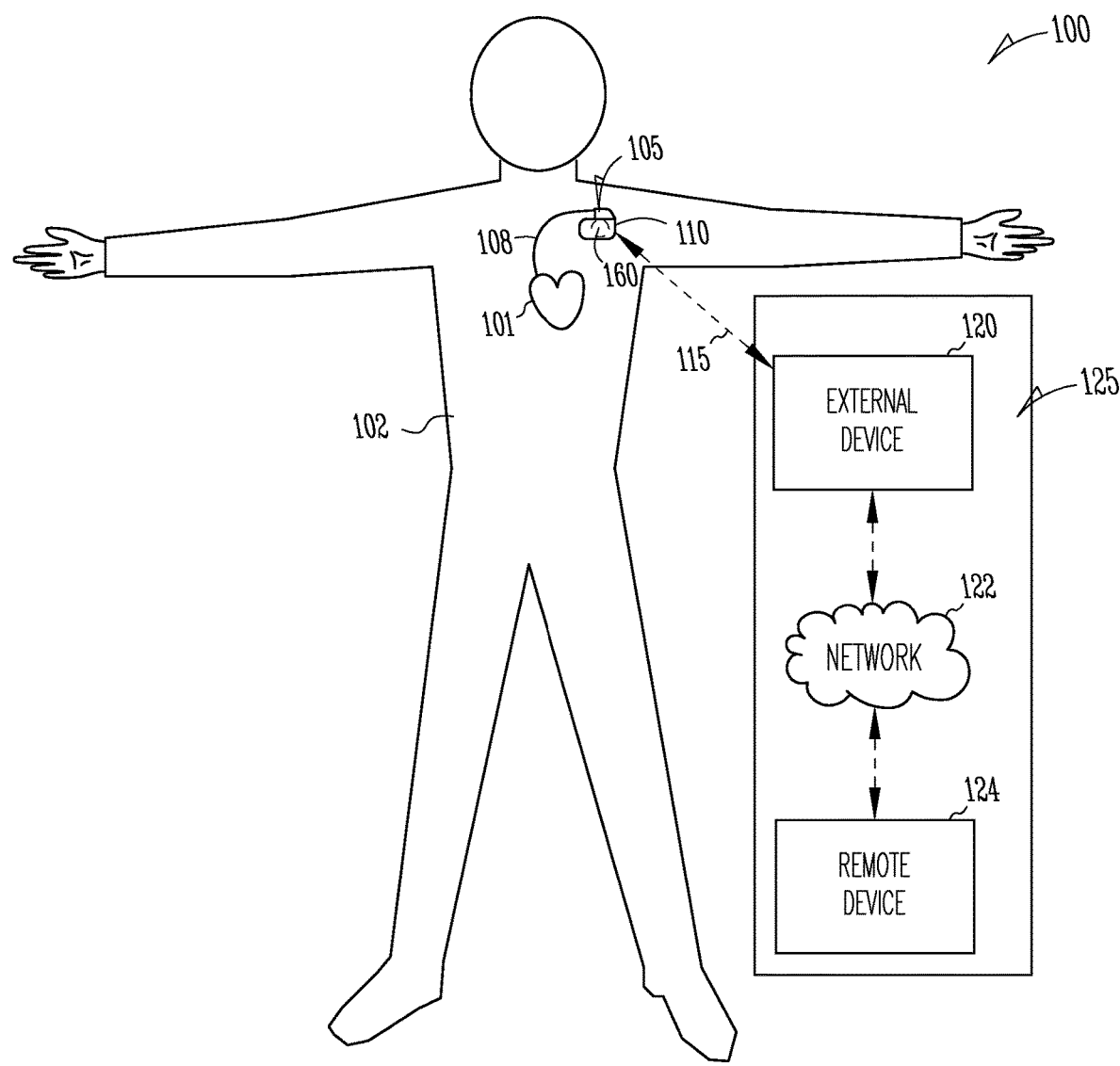
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring and diagnosis of a disease condition. Such activities may be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a data receiver circuit, a control circuit, a communication circuit, and a battery, among other components. The data receiver circuit may sense a physiologic signal, such as by using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiratory rate, tidal volume, respiratory sounds, body weight, or body temperature.

In an example, the AMD 110 may include a HS-based event detector circuit 160 that can detect a physiologic event, such as a cardiac arrhythmia episode, a worsening heart failure (WHF) event, or other cardiovascular or neurological event using heart sounds (HS), among other physiologic signals, sensed from a patient. In an example, the HS-based event detector circuit 160 may receive a sensor signal (e.g., accelerometer signal) sensed from a patient and sampled at a lower sampling rate, and reconstruct a HS signal to have a higher sampling rate using a HS ensemble including portions of the received HS signal over multiple cardiac cycles. A HS metric may be generated using the reconstructed HS segment. The HS-based event detector circuit 160 may detect a cardiac event using the generated HS metric. In an example, at least a portion of the functions of the HS-based event detector circuit 160, such as HS reconstruction or cardiac event detection, may be implemented in and executed by the external system 125.

The AMD 110 may additionally include a therapy unit that may generate and deliver one or more therapies. The therapy may be delivered to the patient 102 via the lead system 108 and the associated electrodes. The therapies may include electrical, magnetic, or other types of therapy. Examples of the anti-arrhythmic therapy may include pacing, cardioversion, defibrillation, neuromodulation, drug therapies, or biological therapies, among other types of therapies. In an example, the therapy unit may be configured to deliver cardiac resynchronization therapy (CRT) or multisite pacing for rectifying dyssynchrony and improving cardiac function in CHF patients. In another example, the therapy unit may be configured to deliver anti-arrhythmic therapy to treat arrhythmias. In yet another example, the therapy unit may be a drug delivery system, such as a drug infusion pump, configured to deliver one or more medications to the patient to treat CHF, arrhythmias, or other physiologic events.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), reconstructing HS signal, detecting a target physiologic event, or delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of WHF events, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the AMD 110. By way of example, alert notifications may include a Web page update, phone or pager call, E-mail, SMS, text or "Instant" message, as well as a message to the patient and a simultaneous direct notification to emergency services and to the clinician. Other alert notifications are possible.

The remote device 124 may additionally include one or more locally configured clients or remote clients securely connected over the network 122 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The network 122 may provide wired or wireless interconnectivity. In an example, thy: network 122 may be based on the Transmission Control Protocol/Internet Protocol (TCP/IP) network communication specification, although other types or combinations of networking implementations are possible. Similarly, other network topologies and arrangements are possible.

The external system 125, such as the external device 120 or the remote device 124, may output the detected physiologic events, such as an event of WHF, to a system user such as the patient or a clinician, or to a process including, for example, an instance of a computer program executable in a microprocessor. The process may include an automated generation or adjustment of therapy and patient management recommendations. The external system 125 may include respective display units for displaying the physiologic signals, or alerts, alarms, emergency calls, or other forms of warnings to signal the detection of a target physiologic event. The external system 125 may additionally display signal analysis results, such as the reconstructed HS segment, the detected physiologic event, or therapy and patient management recommendations, among other information.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
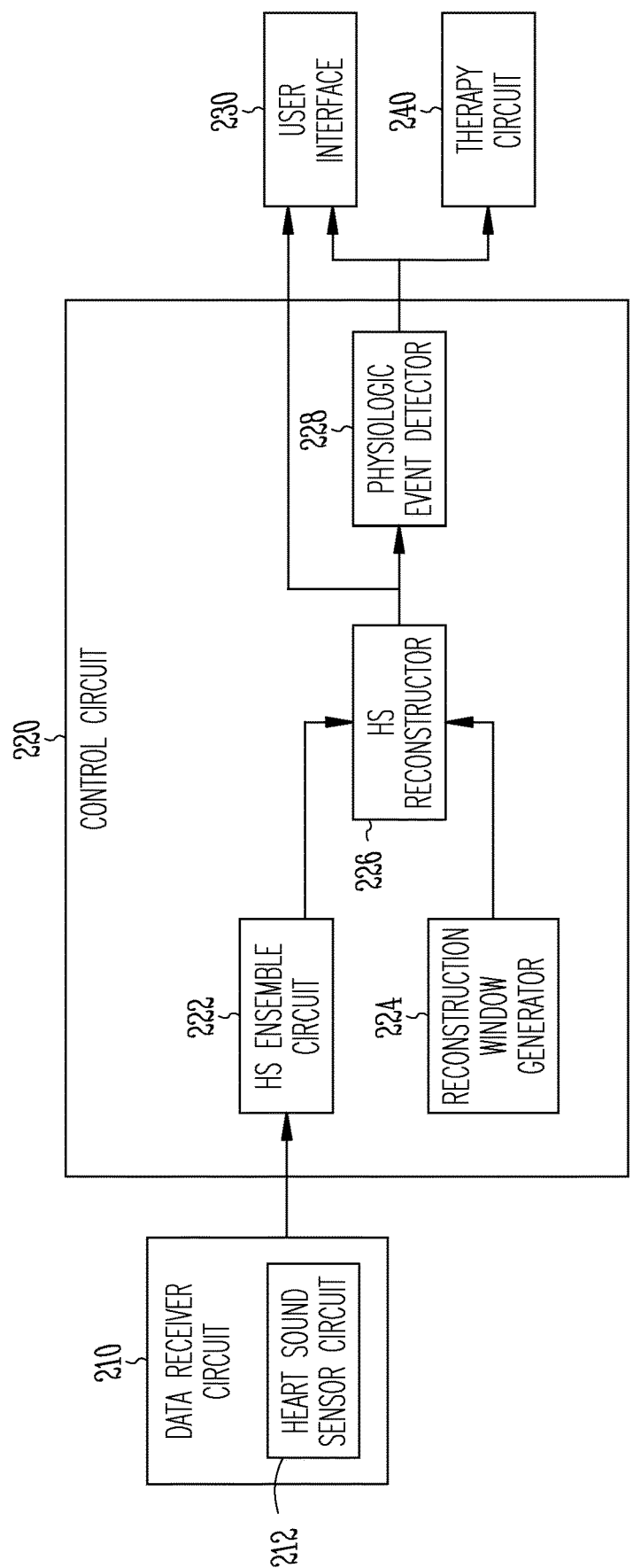
FIG. 2 illustrates generally an example of a physiologic event detection system configured to reconstruct a HS segment and detect a physiologic event using the reconstructed HS segment.

FIG. 2 illustrates generally an example of a physiologic event detection system 200 configured to reconstruct a HS segment and detect a physiologic event, such as a cardiac arrhythmia episode, a worsening heart failure (WHF) event, or other cardiac events, using the reconstructed HS segment. The physiologic event detection system 200 may include one or more of a data receiver circuit 210, a control circuit 220, a user interface 230, and a therapy circuit 240. At least a portion of the physiologic event detection system 200 may be implemented in the AMD 110, the external system 125 such as one or more of the external device 120 or the remote device 124, or distributed between the AMD 110 and the external system 125.

The data receiver circuit 210 may receive physiologic information from a patient. In an example, the data receiver circuit 210 may include a sense amplifier circuit configured to sense a physiologic signal from a patient via a physiologic sensor, such as an implantable, wearable, or otherwise ambulatory sensor or electrodes associated with the patient. The sensor may be incorporated into, or otherwise associated with an ambulatory device such as the AMD 110. In some examples, the physiologic signals sensed from a patient may be stored in a storage device, such as an electronic medical record (EMR) system. The data receiver circuit 210 may receive the physiologic signal from the storage device, such as in response to a user command or a triggering event. Examples of the physiologic signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, heart rate signal, physical activity signal, or posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiologic response to activity, apnea hypopnea index, one or more respiration signals such as a respiratory rate signal or a tidal volume signal, brain natriuretic peptide (BNP), blood panel, sodium and potassium levels, glucose level and other biomarkers and bio-chemical markers, among others. The data receiver circuit 210 may include one or more sub-circuits to digitize, filter, or perform other signal conditioning operations on the received physiologic signal.

In an example, the data receiver circuit 210 may include a heart sound (HS) sensor circuit 212 configured to receive HS information, such as a HS signal sensed from the patient. In an example, the HS sensor circuit 212 may be coupled to a heart sound sensor to sense a body motion/vibration signal indicative of cardiac vibration, which is correlated to or indicative of heart sounds. The HS sensor may take the form of an accelerometer, an acoustic sensor, a microphone, a piezo-based sensor, or other vibrational or acoustic sensors. The accelerometer can be a one-axis, a two-axis, or a three-axis accelerometer. Examples of the accelerometer may include flexible piezoelectric crystal (e.g., quartz) accelerometer or capacitive accelerometer, fabricated using micro electro-mechanical systems (MEMS) technology. The HS sensor may be included in the AMD 110, or disposed on a lead such as a part of the lead system 108. In an example, the accelerometer may sense an epicardial or endocardial acceleration (EA) signal from a portion of a heart, such as on an endocardial or epicardial surface of one of a left ventricle, a right ventricle, a left atrium, or a right atrium. The EA signal may contain components corresponding to various HS components.

The HS sensor circuit 212 may include sensing circuitry configured to sample and digitize the sensed body motion/vibration signal. In an example, the sensing circuitry may operate in a sensing mode characterized by, among other things, a low sampling frequency (Fs1) for acquiring physiologic data. By way of non-limiting example, the heart sound sensor circuit 212 may sample the body motion/vibration signal at approximately 10-20 Hz. For a battery-powered AMD, a lower sampling rate may help conserve battery power.

The sensed body motion/vibration signal, which may also referred to as sensed HS signal hereinafter, may contain other body motion information caused by respiration, physical activities, or posture change, among others. The body motion/vibration signal sampled at a low sampling rate Fs1, which may include at least one of an activity sensing sampling rate, a respiration sensing sampling rate, or a low-power sampling rate. Such a low sampling rate Fs1 may be adequate for detecting certain low-frequency physiologic parameters, such as respiration parameters, physical activity, posture, or some components of cardiac vibration. However, the low-rate body motion/vibration data may not be adequate to produce certain HS metrics, such as timing or amplitude of S2, which have higher frequency contents. These HS metrics can be of clinical significance in cardiac hemodynamics monitoring, detecting cardiac arrhythmia, WHF, or other cardiac events.

The control circuit 220 may reconstruct heart sounds from multiple epochs of low-rate HS signal data. The control circuit 220 be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The control circuit 220 may include circuit sets comprising one or more other circuits or sub-circuits, such as a HS ensemble circuit 222, a reconstruction time window generator 224, a HS reconstructor 226, and a physiologic event detector 228. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The HS ensemble circuit 222 may generate a HS ensemble using a collection of signal portions of the received HS signal, such as signal portions of multiple cardiac cycles. In an example, the data receiver circuit 210 may receive cardiac electrical signals, such as an electrocardiogram (ECG) or an intracardiac electrogram (EGM), that are recorded concurrently with the HS signal. The HS ensemble circuit 222 may detect cardiac cycles as time intervals between two consecutive QRS complexes on the ECG, or between two consecutive cardiac activations on the EGM. The HS ensemble circuit 222 may align the portions (e.g., multiple cardiac cycles) of the received HS signal with respect to respective fiducial points on the multiple cardiac cycles. By way of non-limiting example, the fiducial points may include R waves of the multiple cardiac cycles on the received ECG, or the peaks of the multiple cardiac cycles on the EGM.

In some examples, the HS ensemble circuit 222 may screen the signal portions of the received HS signal, such as HS signal portions of multiple cardiac cycles, and select a subset of HS signal portions that satisfy a specified criterion to form the HS ensemble. The screening criterion may include one or more of patient activity level, heart rate, respiration rate, or time of a day, among other conditions. Examples of HS screening and forming the HS ensemble based on the HS screening are discussed below, such as with reference to FIG. 4.

Figure 3:
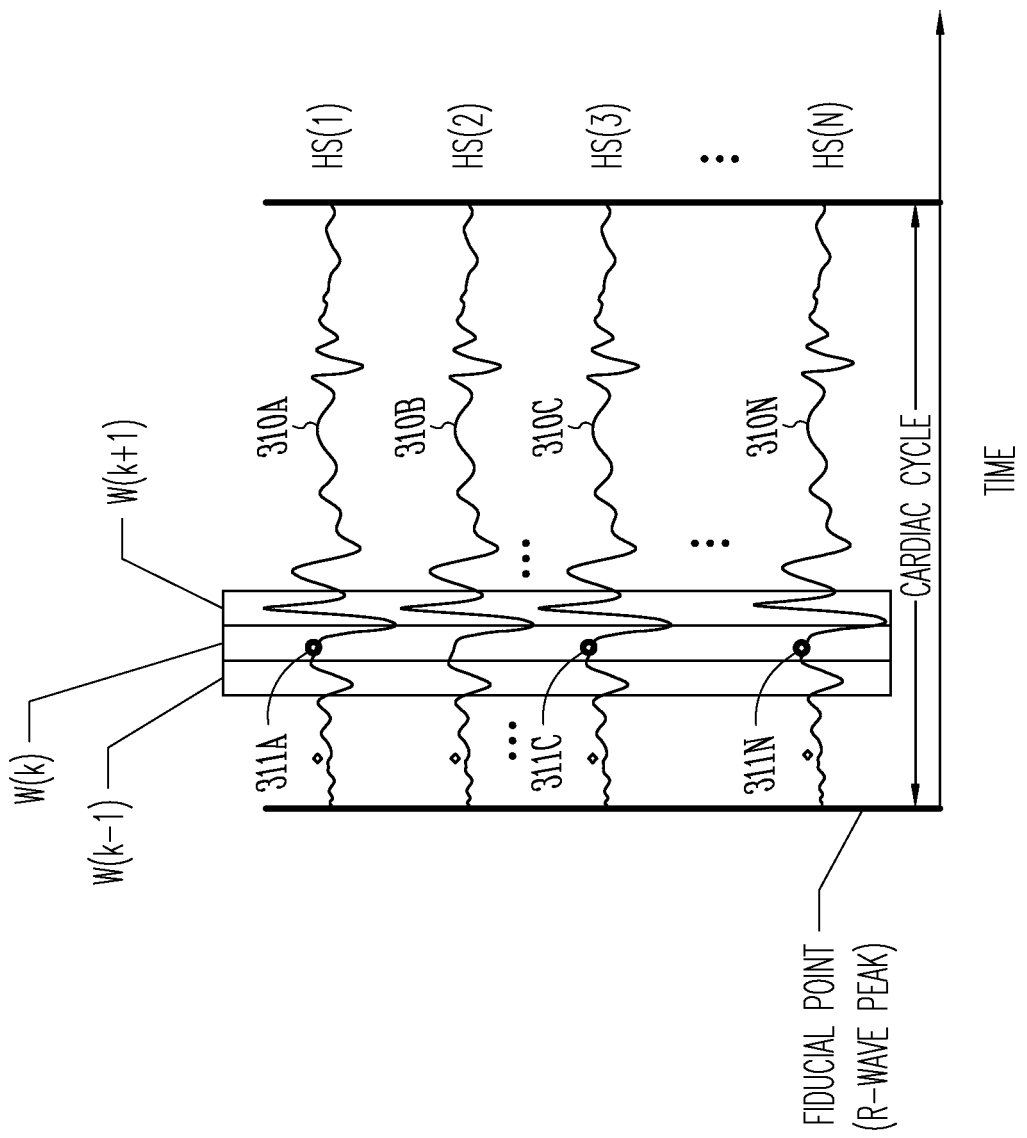
FIG. 3 is graph illustrating an example of a HS ensemble used for reconstructing a HS segment.

The reconstruction time window generator 224 may produce a plurality of reconstruction time windows $\{W(i)\}$. Data samples of the HS ensemble that fall within a reconstruction time window may be used to reconstruct a HS data sample corresponding to the corresponding reconstruction time window. The reconstruction time windows may be produced based on a specified sampling rate (Fs2) for the reconstructed HS segment. In an example, Fs2 is higher than the sampling frequency Fs1 of the HS signal produced by the HS sensor circuit 212. In an example, the reconstruction time windows each have a duration Dw inversely proportional to Fs2. In an example, $Dw=1/Fs2$. If $Fs2=200$ Hz, then the reconstruction time window duration $Dw=5$ milliseconds (msec). In an example, the reconstruction time windows are consecutive and do not overlap each other. In another example, the neighboring reconstruction time windows at least partly overlap by a specified time or percentage of window length (e.g., 50% overlap). Examples of aligning the HS ensemble including portions of the received HS signal over multiple cardiac cycles, and applying the reconstruction time windows to the aligned HS ensemble, are discussed below, as illustrated in FIG. 3.

The HS reconstructor 226 may reconstruct a HS segment to have the sampling rate Fs2 using the aligned HS ensemble. In an example, one reconstructed HS data sample may be generated within each reconstruction time window using a central tendency of the HS data samples of the aligned HS ensemble that fall within the corresponding reconstruction time window. Examples of central tendency may include mean, median, mode, or other measures. Alternatively, the reconstructed HS data sample at each reconstruction time window may be computed using a weighted average of the HS data samples of the aligned HS ensemble that fall within the corresponding reconstruction time window. In an example, the weigh factor may be determined based on the timing of the HS data samples within the reconstruction time window, such that the data sample that is closer to the center of the reconstruction time window may be assigned with a larger weight. In another example, the weigh factor may be determined based on the chronological order of the HS signal portions in the HS ensemble. For example, the data sample that is associated with a more recent HS signal portion (e.g., a cardiac cycle) may be assigned with a larger weight. In another example, the weight factor may be determined based on the associated heart rate, such that the data sample in the cardiac cycles that are closer to the mean of all cardiac cycles may be assigned with a larger weight. Because one reconstructed HS data sample is generated for each reconstruction time window having a window duration of $Dw=1/Fs2$ second, the data rate for the reconstructed HS segment is Fs2 samples per second, or Fs2 Hz. As such, the HS reconstructor 226 effectually upsamples the received low-rate HS signal (at a sampling rate of Fs1) to Fs2.

The HS reconstructor 226 may reconstruct the HS signal through the entire duration of the HS ensemble (e.g., a complete cardiac cycle). Alternatively, the HS reconstructor 226 may reconstruct one or more HS segments, such as an S1 segment, an S2 segment, an S3 segment, or an S4 segment within a cardiac cycle. In an example, the HS reconstructor 226 may detect from each HS signal portion of the HS ensemble a HS segment of interest (e.g., S1), form an ensembles of the HS segment (e.g., S1 ensemble), and reconstruct that HS segment (e.g., reconstructed S1) using the ensemble of the same HS segment. In another example, the HS reconstructor 226 may reconstruct the HS signal through the complete cardiac cycle, and then detect and extract a HS segment of interest (e.g., S1) from the reconstructed HS segment.

In some example, the HS reconstructor 226 may reconstruct two or more HS segments, including a first HS segment at a sampling rate Fs2, and a second HS segment at a distinct sampling rate Fs3 different from Fs1 and Fs2. Such selective reconstruction of different HS segments at distinct sampling rates can be advantageous, as the HS metrics generated from different HS segments may have different temporal resolution requirements. In a specific example, the HS reconstructor 226 may reconstruct an S1 segment to have a sampling rate of Fs2, and reconstruct an S2 segment to have a sampling rate Fs3 greater than Fs2. Because S2 generally has higher frequency content (e.g., approximately 20-70 Hz) than S1 (e.g., approximately 10-50 Hz), a higher sampling rate Fs3, which corresponds to a finer temporal resolution of the reconstructed S2, may improve detection accuracy of S2-based HS metrics, such as S2 peak or S2 timing.

The physiologic event detector 228 may detect a target physiologic event using the reconstructed HS segment produced by the HS reconstructor 226. The physiologic event detector 228 may include a filter circuit to remove one or more of low-frequency signal baseline drift, high frequency noise, or certain frequency contents introduced during HS reconstruction (e.g., reconstruction jitters). In an example, the reconstructed HS segment may be band-pass filtered to a frequency range of approximately 5-90 Hz, or approximately 9-90 Hz. In an example, the filter may include a double or higher-order differentiator configured to calculate a double or higher-order differentiation of the heart sound signal. The physiologic event detector 228 may compute an ensemble average of the reconstructed HS segment over multiple cardiac cycles, or over a specified time period, and detect one or more HS components, including a first (S1) heart sound, a second (S2) heart sound, a third (S3) heart sound, or a fourth (S4) heart sound using respective time windows. The physiologic event detector 228 may generate a HS metric using the detected HS components. Examples of the HS metric may include an intensity (e.g., amplitude or signal energy under the curve) of a HS component, or one or more HS-based cardiac timing intervals, such as a pre-ejection period (PEP) such as measured between the onset of the QRS to the S1 heart sound, a systolic timing interval (STI) such as measured between the onset of the QRS complex on the ECG to the S2 heart sound, a left-ventricular ejection time (LVET) such as measured as an interval between S1 and S2 heart sounds, or a diastolic timing interval (DTI) such as measured between the S2 heart sound and the onset of the subsequent QRS complex on the ECG, among others. These HS-based cardiac timing intervals may be correlated with cardiac contractility or cardiac diastolic function of the heart. The HS metrics may further include PEP/LVET ratio, STI/DTI ratio, STI/cycle length (CL) ratio, or DTI/CL ratio, or other composite metrics.

The physiologic event detector 228 may be configured to detect a target physiologic event using, among other physiologic information acquired from the patient, the HS metrics generated from the reconstructed HS segment. In an example, the physiologic event detector 228 may generate a cardiac function indicator indicating myocardial contractility, cardiac synchrony, and cardiac hemodynamics, using one or more HS metrics. In an example, the physiologic event detector 228 may detect a cardiac arrhythmia episode, or distinguish between different arrhythmias (e.g., atrial tachyarrhythmia, supraventricular tachyarrhythmia, or ventricular tachyarrhythmia) using one or more of S1 intensity, S2 intensity, or a measure of STI. For example, a reduction in S1 intensity may be indicative of reduced cardiac contractility, and a reduction in S2 intensity may be indicative of reduced cardiac output, both of which may be used to detect cardiac arrhythmias and deterioration of cardiac hemodynamics during arrhythmia. In another example, the HS metrics, such as S3 intensity, may be used to detect WHF. An increase in S3 intensity indicates reduced ventricular compliance and deteriorating diastolic function, signifying occurrence of WHF. Additionally or alternatively, a reduction in S1 intensity, or a reduction in STI may indicate poor cardiac contractility or reduced electromechanical coupling, which signifies occurrence of WHF. The physiologic event detector 228 may additionally or alternatively detect respiratory, renal, neurological, among other medical conditions, based on the HS metrics generated from the reconstructed HS segment.

The user interface 230 may include an input unit and an output unit. In an example, at least a portion of the user interface 230 may be implemented in the external system 125. The input unit may receive user input for programming the data receiver circuit 210 and the control circuit 220, such as parameters for sensing the HS signal, reconstructing the HS segment, generating a HS metric, or detecting a physiologic event. The input unit may include a keyboard, on-screen keyboard, mouse, trackball, touchpad, touch-screen, or other pointing or navigating devices. The output unit may include a display for displaying the sensed HS signal, the reconstructed HS segment, the generated HS metrics, information about the detected physiologic events, and any intermediate measurements or computations, among others. The output unit may also present to a user, such as via a display unit, the therapy titration protocol and recommended therapy, including a change of parameters in the therapy provided by an implanted device, the prescription to get a device implanted, the initiation or change in a drug therapy, or other treatment options of a patient. The output unit may include a printer for printing hard copies of information that may be displayed on a display unit. The signals and information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the detected medical events.

The therapy circuit 240 may be configured to deliver a therapy to the patient, such as in response to the detected physiologic event. The therapy may be preventive or therapeutic in nature such as to modify, restore, or improve patient neural, cardiac, or respiratory functions. Examples of the therapy may include electrostimulation therapy delivered to the heart, a nerve tissue, other target tissues, a cardioversion therapy, a defibrillation therapy, or drug therapy including delivering drug to the patient. In some examples, the therapy circuit 240 may modify an existing therapy, such as adjust a stimulation parameter or drug dosage.

FIG. 3 is graph illustrating an example of a HS ensemble used for reconstructing a HS segment, such as by using portions of the physiologic event detection system 200. The HS ensemble includes multiple HS signal portions, 310A, 310B, . . . , 310N, each taken from a HS signal in different cardiac cycles. In the illustrated example, the HS signal portions 310A, 310B, . . . , 310N are a subset of a HS signals portions that pass a HS screening test, such that the signal portions 310A, 310B, . . . , 310N have substantially the same cardiac cycle length within a specified margin (e.g., +/−100 msec), or substantially the same heart rate within a specified margin (e.g., +/−5 beats per minute, bpm). The HS signal portions 310A, 310B, . . . , 310N may be aligned with respect to the R waves on an ECG signal on the corresponding cardiac cycles. The ECG signal can be concurrently recorded with the HS. The aligned HS signal portions 310A, 310B, . . . , 310N form an HS ensemble.

A series of consecutive reconstruction time window {W(i)}, such as generated by the reconstruction time window generator 224, may be applied to aligned HS ensemble. In an example, the sensed HS signal, and thus the HS signal portions 310A, 310B, . . . , 310N, are sampled at a data rate of Fs1. To reconstruct the HS segment to have a higher sampling rate Fs2 (greater than Fs1), the reconstruction time window length Dw may be chosen to be 1/Fs2. Data samples from all HS signal portions of the HS ensemble that fall within the reconstruction time window W(k) may be used to determine a reconstruction HS sample at the time of W(k).

Because HS signal portions 310A, 310B, . . . , 310N are sampled at the rate Fs1 lower than Fs2, in some cases, only some but not all of the HS signal portions in the HS ensemble have data samples falling with a reconstruction time. For example, in FIG. 3, the HS signal portions 310A, 310C, and 310N each have respective data sample 311A, 311C, 311N falling within the window W(k), but no data sample from the HS signal portion 310B falls into the window W(k). A central tendency of all those HS data samples in the window W(k) may be determined to be the reconstructed HS sample at the time corresponding to W(k). In case no HS data sample falls within W(k), more HS signal portions may be collected and included in the HS ensemble. Alternatively, a data interpolation may be performed using the reconstructed HS data at one or more neighboring reconstruction time windows (e.g., W(k−1) and W(k+1)). Because the temporal resolution of the reconstruction time windows is 1/Fs2, the reconstructed HS segment also has a temporal resolution of 1/Fs2, or a reconstructed sampling rate of Fs Hz.

Figure 4:
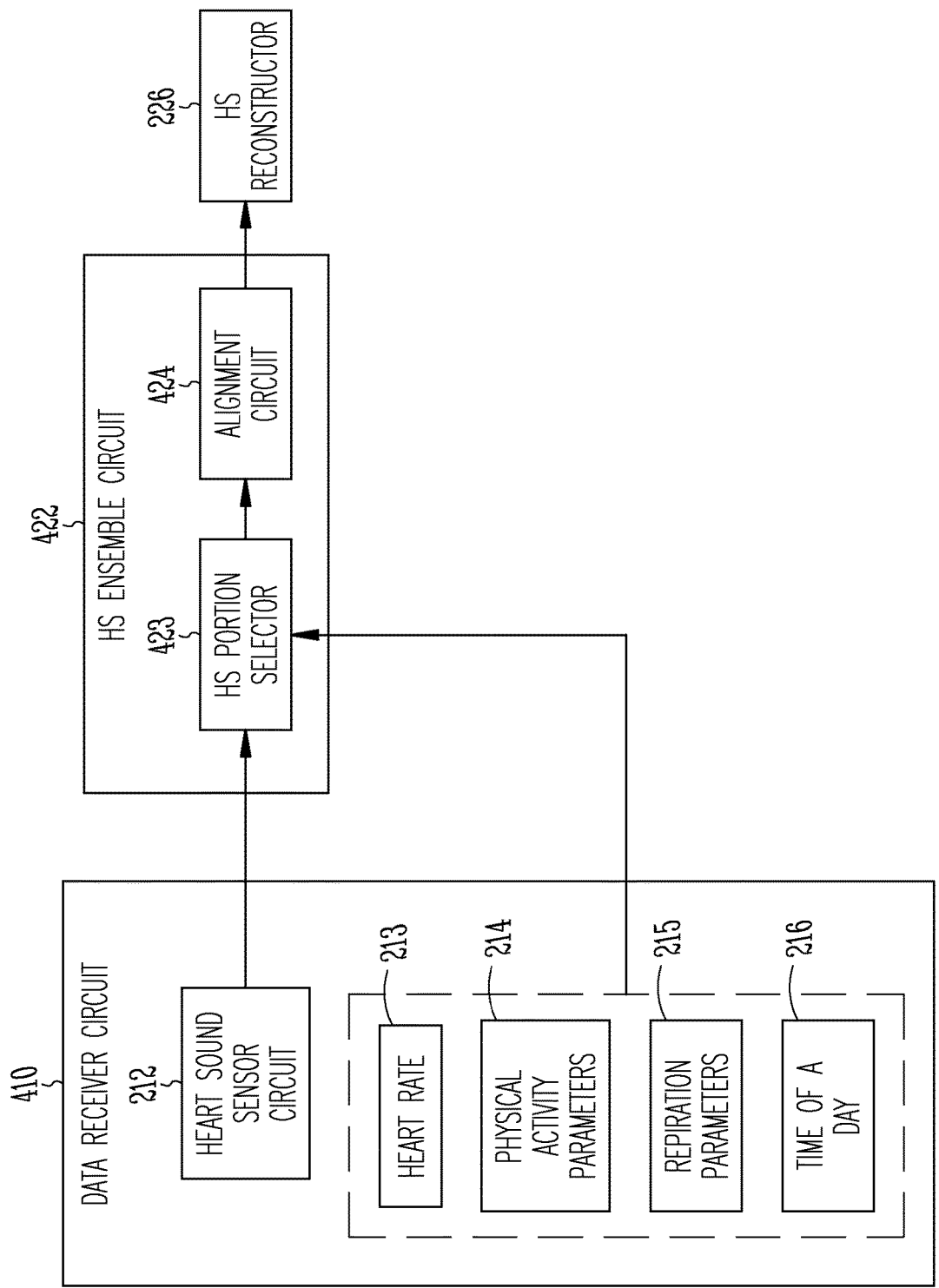
FIG. 4 illustrates generally an example of a portion of a HS reconstruction system.

FIG. 4 illustrates generally an example of a HS reconstruction system 400, which may be an embodiment of a portion of the physiologic event detection system 200. The HS reconstruction system 400 includes a data receiver circuit 410 configured to receive physiologic information from a patient. The data receive circuit 410 is an embodiment of the data receiver circuit 210 illustrated in FIG. 2, which includes a heart sound senor circuit 212 configured to sense a HS signal sampled at a low sampling rate Fs1, or otherwise to receive such a low-rate HS signal stored in a storage device. The data receiver circuit 410 may additionally receive information about patient conditions acquired concurrently with the HS signal. By way of example and not limitation, such additional information may include one or more of a heart rate 213, physical activity parameters 214, or respiration parameters 215. Examples of the physical activity parameters may include physical activity level. Examples of the respiration parameters may include respiratory rate, tidal volume, rapid-shallow breathing index (RSBI) computed as a ratio of a respiratory rate measurement to a tidal volume measurement, respiratory sounds, etc. Such additional information may be stored in a storage device along with the HS signal. Alternatively, the additional information may be concurrently sensed by physiologic sensors associated with the patient. In an example, the physical activity may be sensed using an accelerometer sensor, and the respiration parameters may be sensed using a thoracic impedance sensor. Additionally or alternatively, information about time of a day 216 may be acquired and used for reconstructing a HS segment.

The HS reconstruction system 400 may use one or more of the heart rate 213, the physical activity parameters 214, the respiration parameters 215, or the time of day 216 to screen the HS signal portions taken from the received HS signal. The HS ensemble circuit 422, which is an embodiment of the HS ensemble circuit 222 illustrated in FIG. 2, may include a HS portion selector 423 configured to select, from the HS portions of multiple cardiac cycles, a subset of HS portions with the corresponding heart rates or cycle lengths falling within a specified range, such as substantially the same cycle length within a margin of +/−100 msec, or substantially the same heart rate within a margin of +/−5 bpm. Additionally or alternatively, the HS portion selector 423 may select a subset of HS portions with the corresponding physical activity levels falling within a specified range, such as substantially the same physical activity level within a specified margin, or a subset of HS portions with the corresponding respiratory rates falling within a specified range, such as substantially the same respiratory rate within a specified margin. In some examples, the data receiver circuit may be configured to receive the HS signal sensed from the subject during a specified time period of a day, or that the HS portion selector 423 may select a subset of HS portions that are sensed during substantially the same time period of a day within a specified margin. The HS data around the same time of day from a number of days may be used to increase the amount of data samples for reconstructing a heart sound segment.

The alignment circuit 424 may align the selected subset of the HS signal portions form the HS ensemble. The HS reconstructor 226 may reconstruct the HS by applying the reconstruction time windows to the aligned HS ensemble, as discussed above in reference to FIGS. 2-3.

Figure 5:
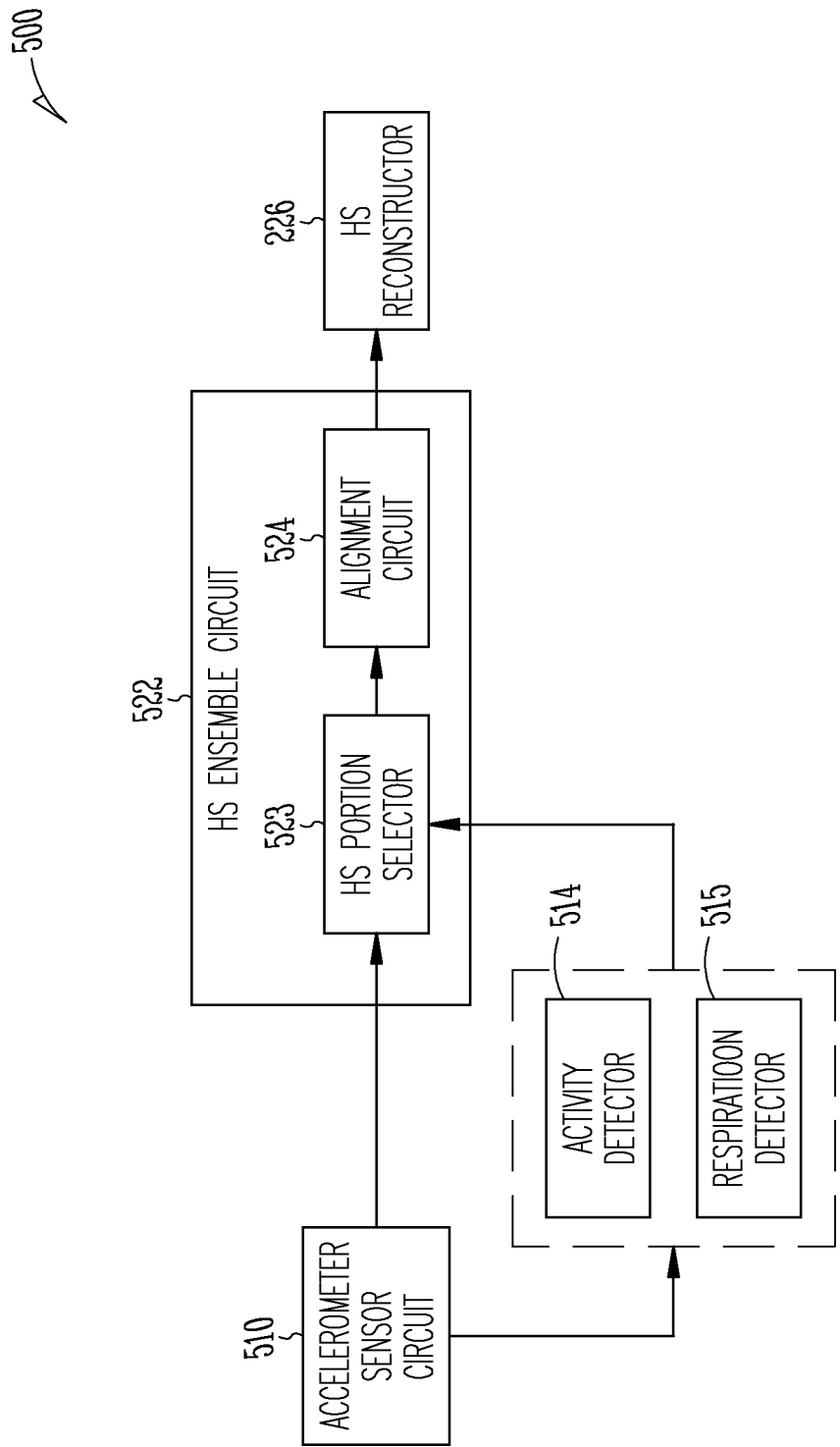
FIG. 5 illustrates generally another example of a portion of a HS reconstruction system.

FIG. 5 illustrates generally an example of a portion of a HS reconstruction system 500, which may be an embodiment of a portion of the physiologic event detection system 200. The HS reconstruction system 500 includes an accelerometer sensor circuit 510 configured to sense an accelerometer signal from a patient. The accelerometer sensor may be included in an ambulatory device such as the AMD 110, or disposed on a lead such as a part of the lead system 108. The accelerometer may be configured to sense body motion, such as caused by physical activity, respiration, or cardiac vibration. In an example, the accelerometer sensor circuit 510 may be configured to operate in sensing mode to detect relatively low-frequency physiologic parameters such as physical activity level and/or respiration rate. Under such sensing mode, the accelerometer sensor circuit 510 acquires body motion/vibration signal at a low sampling rate Fs1, such as in a range of approximately 10-20 Hz. An activity detector 514 may detect from the sensed acceleration signal information about physical activity level. Additionally or alternatively, a respiration detector 515 may detect from the sensed acceleration signal information about the respiratory rate.

The HS ensemble circuit 522, which is an embodiment of the HS ensemble circuit 222 illustrated in FIG. 2, may include a HS portion selector 523 that may generate, from the low-rate acceleration signal provided by the accelerometer sensor circuit 510, a plurality of candidate HS portions of multiple cardiac cycles. In contrast to the HS reconstruction system 400 in FIG. 4, in which case the low-rate HS signal and patient conditions (e.g., the physical activity parameters 214 and the respiration parameters 215) may be sensed using different sensors, the HS reconstruction system 500 recycles the same accelerometer sensor signal that is also used for detecting low-frequency physiologic parameters such as respiratory rate and physical activity. The recycling of acceleration signal may not only simplify the system complexity and reduce cost, but may also help save storage space and communication bandwidth for handling the low-rate acceleration data. The HS portion selector 523 may select, from the HS portions of multiple cardiac cycles, a subset of HS portions with the corresponding activity level (as produced by the activity detector 514), and/or with the corresponding respiratory rate (as produced by the respiration detector 515) falling within respectively specified ranges. In an example, HS portions corresponding to substantially the same activity level, and/or substantially the same respiratory rate, within respectively specified margins, are selected to form the HS ensemble. The alignment circuit 524 may align the selected subset of the HS signal portions form the HS ensemble. The HS reconstructor 226 may reconstruct the HS by applying the reconstruction time windows to the aligned HS ensemble, as discussed above in reference to FIGS. 2-4.

Figure 6:
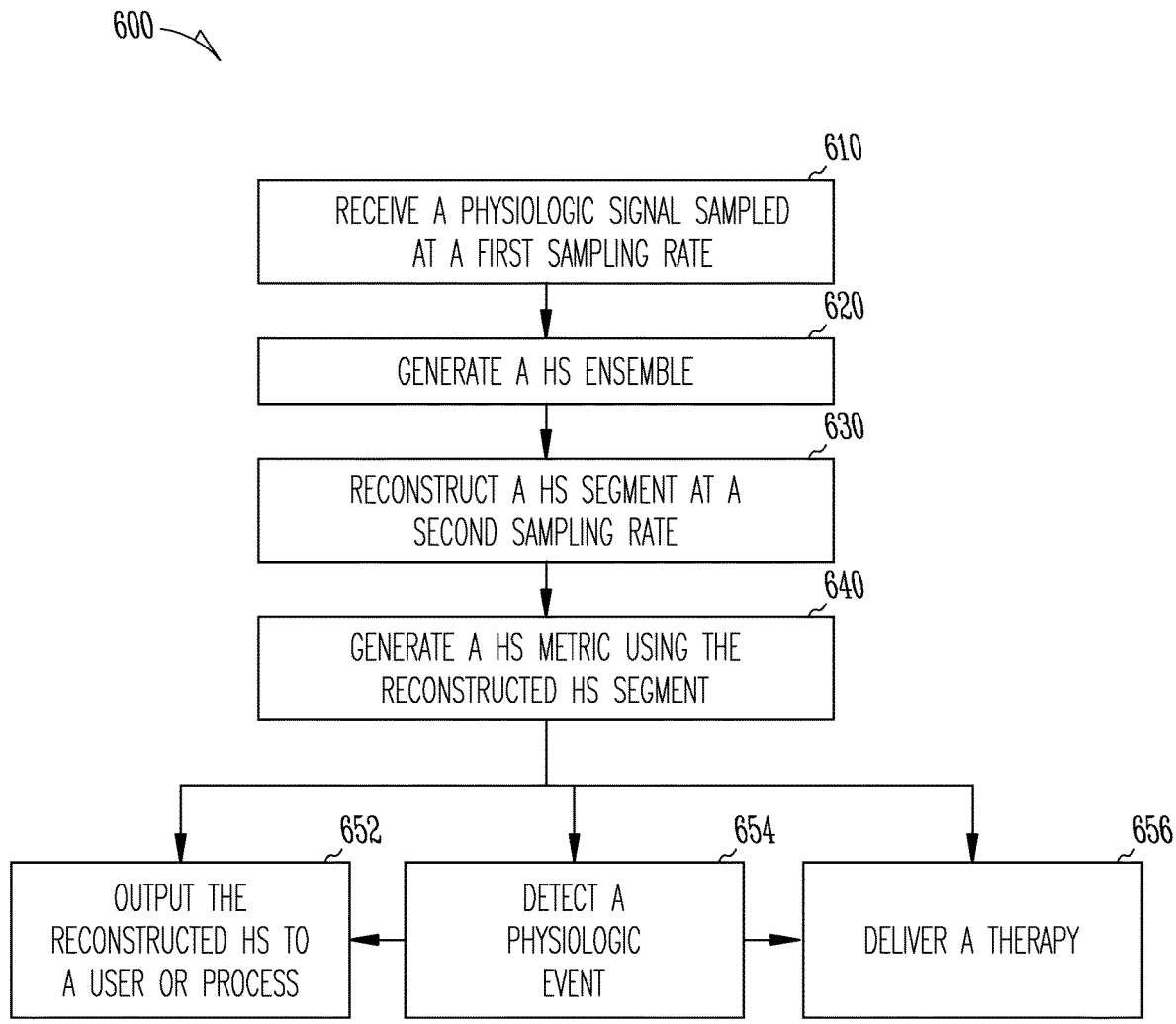
FIG. 6 illustrates generally an example of a method for sensing heart sounds in a subject.

FIG. 6 illustrates generally an example of a method 600 for sensing heart sounds in a subject. The method 600 may be implemented and executed in an ambulatory medical device such as an implantable or wearable medical device, or in a remote patient management system. In an example, the method 600 may be implemented in and executed by the cardiac arrhythmia detection circuit 160 in the AMD 110, the external system 130, or the physiologic event detection system 200.

The method 600 commences at 610, where a physiologic signal may be received from a data storage device, or sensed from a physiologic sensor circuit. The physiologic signal may include a cardiac electrical signal such as an electrocardiography (ECG) or an intracardiac electrogram (EGM). The physiologic signals may additionally or alternatively include signals indicative of cardiac mechanical activity, including thoracic or cardiac impedance signal, arterial pressure signal, pulmonary artery pressure signal, left atrial pressure signal, RV pressure signal, LV pressure signal, heart sounds or endocardial acceleration signal, physiologic response to activity, apnea hypopnea index, one or more respiration signals such as a respiration rate signal or a tidal volume signal, among others.

In an example, the physiologic signal may include a body motion/vibration signal, such as sensed from a subject using the sensor circuit 212 or the accelerometer sensor circuit 510. The body motion may be caused by one or more of physical activity, respiration, cardiac vibrations, etc. As the body motion/vibration signal is used to reconstruct HS, the body motion/vibration signal is also referred to as received HS signal hereinafter. However, it is to be recognized that the body motion/vibration signal may also contain motion information caused by respiration, physical activities, or posture change, among others. The body motion/vibration signal may be sensed using a low sampling rate Fs1, such as in a range of approximately 10-20 Hz. Such a sampling rate may be adequate to preserve frequency contents of low-frequency physiologic parameters such as physical activity level and/or respiration rate. In an example, physical activity level may be detected from the sensed body motion/vibration signal, such as using the activity detector 514. Additionally or alternatively, respiration parameters such as respiratory rate may be detected from the sensed body motion/vibration signal, such as using the respiration detector 515.

At 620, a HS ensemble including portions of the received HS signal over multiple cardiac cycles, such as using the HS ensemble circuit 222. The portions of the HS signal, such as HS signal in multiple cardiac cycles, may be extracted from and received HS signal. The HS portions may then be aligned with respect to respective fiducial points on the multiple cardiac cycles, such as the R waves of the multiple cardiac cycles on the received ECG concurrently recorded with the HS signal. The aligned HS portions thus form a HS ensemble. In some examples, the HS signal portions (e.g., over multiple cardiac cycles) may be screened, and a subset of the HS signal portions that pass a screening criterion are selected to form the HS ensemble. The screening criterion may include one or more of patient activity level, heart rate, respiration rate, or time of a day, among other conditions. In an example, the HS ensemble includes a subset of HS portions corresponding to substantially the same cycle length within a margin of +/−100 msec, or substantially the same heart rate within a margin of +/−5 bpm. In another example, the HS ensemble includes a subset of HS portions corresponding to substantially the same physical activity level within a specified margin, or a subset of HS portions corresponding to substantially the same respiratory rate within a specified margin. In yet another example, the HS ensemble includes a subset of HS portions that are sensed during substantially the same time of a day within a specified margin.

At 630, a HS segment may be reconstructed to have a second sampling rate Fs2 using the HS ensemble produced at step 620, such as using the HS reconstructor 226. In an example, Fs2 is higher than the sampling frequency Fs1 of the HS signal (or the body motion/vibration signal) received at 610. Reconstruction may be performed within each of a series of consecutive reconstruction time windows, such as the exemplary windows {W(i)} as illustrated in FIG. 3. One reconstructed HS data sample may be generated within each reconstruction time window using a central tendency of the HS data samples of the aligned HS ensemble that fall within the corresponding reconstruction time window. In case no HS data sample falls within a reconstruction time window, more HS signal portions may be collected and included in the HS ensemble. Alternatively, a data interpolation may be performed using the reconstructed HS data at one or more neighboring reconstruction time windows. Each window W(i) may have a duration Dw inversely proportional to Fs2. In an example, Dw=1/Fs2. Because the temporal resolution of the reconstructed HS segment has a temporal resolution of 1/Fs2, the reconstructed HS segment has a data rate of Fs2, which is higher than the received HS signal.

The HS reconstruction at 630 may be performed through the entire duration (e.g., a complete cardia cycle) of the HS ensemble, or one or more HS segments, such as an S1 segment, an S2 segment, an S3 segment, or an S4 segment within a cardiac cycle. In an example, different HS segments may be reconstructed respectively to different sampling rates. For example, S2 segment may be reconstructed at a higher sampling rate than a S1 segment. This may improve the detection accuracy of detecting high-frequency S2 metrics such as S2 peak or S2 timing.

At 640, a HS metric may be generated using the reconstructed HS segment. In an example, the reconstructed HS segment may be filtered to remove, for example, one or more of low-frequency signal baseline drift, high frequency noise, or certain frequency contents introduced during HS reconstruction (e.g., reconstruction jitters). A HS metric may be generated using the filtered reconstructed HS segment. Examples of the HS metric may include an intensity (e.g., amplitude or signal energy under the curve) of a HS component, or one or more HS-based cardiac timing intervals.

The reconstructed HS segments produced at 630, and/or the HS metric generated at 640, may be provided to a user or a process, such as one or more of 652, 654, or 656. At 652, the reconstructed HS segments and/or the HS metric generated therefrom may be output to a user or a process, such as via the user interface 230 illustrated in FIG. 2. In an example, information may be displayed on a display, including the sensed HS signal, the reconstructed HS segment, the generated HS metrics, or information about a physiologic event detected using the reconstructed HS, among others. Additionally or alternatively, a hard copy of the detection information may be generated.

At 654, a physiologic event may be detected using the HS metric generated from the reconstructed HS segment, such as using the physiologic event detector 228. The physiologic event may include an indicator of myocardial contractility, cardiac synchrony, and cardiac hemodynamics, a cardiac arrhythmia episode, or a WHF event. In some examples, the HS metric may be used together with other sensor information to detect respiratory, renal, neurological, among other medical conditions, based on the HS metrics generated from the reconstructed HS segment. In some examples, based on the detection of the physiologic event, a recommendation may be generated and provided to the user at 652. The recommendation may include one or more of further diagnostic tests to be performed, adjustment of one or more parameters for detecting the physiologic event, or therapy to be delivered or adjustment of one or more therapy parameters. The system user may review and adjudicate the detected physiologic event, and reprogram one or more detection or therapy parameters, such as using the user interface 230.

At 656, a therapy may be delivered to the patient in response to the detected physiologic event, such as via the therapy circuit 240 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia, such as modify patient follow-up schedule, or adjust a stimulation parameter or drug dosage.

Figure 7:
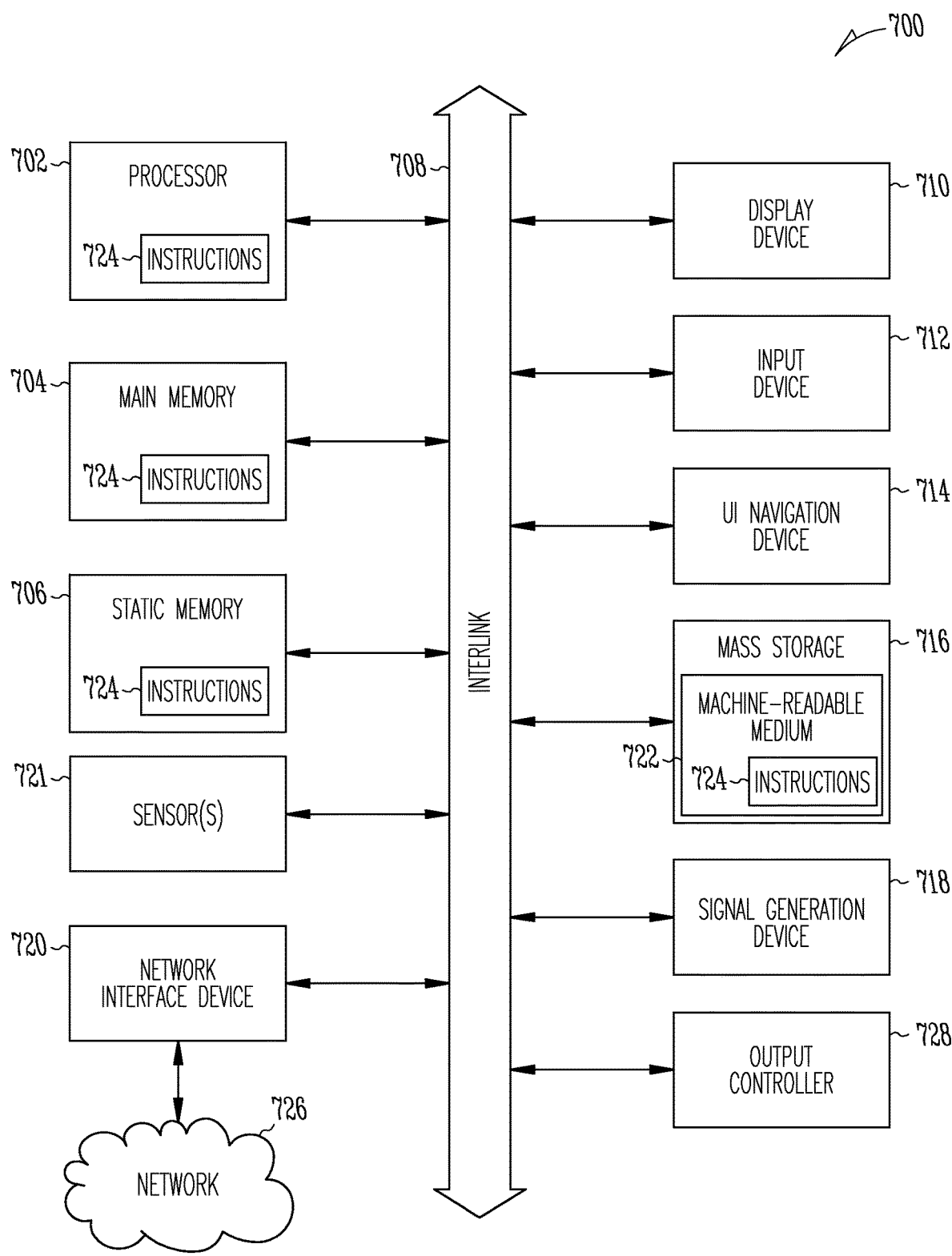
FIG. 7 illustrates generally a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the IMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine-readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 724 may further be transmitted or received over a communication network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communication network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for producing a high-fidelity heart sound signal from low-frequency acceleration information, comprising:
   a data receiver circuit configured to receive acceleration information from a patient sensed at a first sampling rate; and
   a control circuit configured to:
      align portions of the received acceleration information over multiple cardiac cycles with respect to respective fiducial points;
      generate a heart sound (HS) ensemble including the aligned portions of the received acceleration information; and
      reconstruct a HS segment of the acceleration information including computing representative HS values using the generated HS ensemble corresponding to the multiple cardiac cycles, the reconstructed HS segment having a second sampling rate higher than the first sampling rate.

2. The system of claim 1,
   wherein the data receiver circuit is coupled to an accelerometer configured to sense the acceleration information including at least one of an activity signal, a body motion signal, or a respiration signal at the first sampling rate.

3. The system of claim 1, wherein the reconstructed HS segment includes one or more of an S1 segment, an S2 segment, an S3 segment, or an S4 segment within a cardiac cycle, and wherein the control circuit is configured to reconstruct a first HS segment to have the second sampling rate, and reconstruct a second HS segment to have a third sampling rate different than the first and second sampling rates, the first and second HS segments representing different segments of a cardiac cycle.

4. The system of claim 1, wherein the respective fiducial points include respective R waves of an electrocardiogram signal within the multiple cardiac cycles.

5. The system of claim 1, wherein the control circuit is configured to:
   produce reconstruction time windows each having a duration inversely proportional to the second sampling rate; and
   reconstruct the HS segment using HS data of the generated HS ensemble falling within the produced reconstruction time windows.

6. The system of claim 5, wherein the control circuit is configured to reconstruct the HS segment using a central tendency of the HS data within each of the produced reconstruction time windows.

7. The system of claim 1, wherein the data receiver circuit is configured to receive heart rates (HRs) or cycle lengths (CLs) measured concurrently with the acceleration information, and the control circuit is configured to generate the HS ensemble including portions of the received acceleration information over multiple cardiac cycles with corresponding received HRs or CLs falling within a specified range.

8. The system of claim 1, wherein the data receiver circuit is configured to receive physical activity level sensed concurrently with the acceleration information, and the control circuit is configured to generate the HS ensemble including portions of the received acceleration information over multiple cardiac cycles with corresponding received physical activity level falling within a specified activity range.

9. The system of claim 1, wherein the data receiver circuit is configured to receive respiratory rates sensed concurrently with the acceleration information, and the control circuit is configured to generate the HS ensemble including portions of the received acceleration information over multiple cardiac cycles with corresponding received respiratory rates falling within a specified respiratory rate range.

10. The system of claim 1, wherein the data receiver circuit is configured to receive information about time of a day during which the acceleration information is sensed, and the control circuit is configured to generate the HS ensemble including portions of the received acceleration information over multiple cardiac cycles corresponding to substantially the same time of a day.

11. The system of claim 1, wherein the data receiver circuit is coupled to an accelerometer to sense a body motion signal at the first sampling rate, and the control circuit is configured to:
   detect one or more of a physical activity level or a respiratory rate using the sensed body motion signal;
   identify portions of the sensed body motion signal corresponding to the detected physical activity level falling within a specified physical activity range or the detected respiratory rate falling within a specified respiratory rate range; and
   generate the HS ensemble including multiple cardiac cycles of the identified portions of the sensed body motion signal.

12. The system of claim 1, wherein the control circuit is configured to generate a HS metric including an intensity metric or a timing metric of one or more of a first (S1), second (S2), third (S3), or fourth (S4) heart sound component measured from the reconstructed HS segment, and the system comprises:
   a physiologic event detector configured to detect a cardiac event using the generated HS metric; and
   a therapy circuit configured to initiate or adjust a therapy in response to the detected cardiac event.

13. The system of claim 1, wherein the reconstructed HS segment includes one or more of an S1 segment, an S2 segment, an S3 segment, or an S4 segment within a cardiac cycle.

14. A method for producing a high-fidelity heart sound signal from low-frequency acceleration information, comprising:
- receiving acceleration information from a patient sensed at a first sampling rate;
- aligning portions of the received acceleration information over multiple cardiac cycles with respect to respective fiducial points;
- generating a heart sound (HS) ensemble including the aligned portions of the received acceleration information;
- reconstructing a HS segment of the acceleration information including computing representative HS values using the generated HS ensemble corresponding to the multiple cardiac cycles, the reconstructed HS segment having a second sampling rate higher than the first sampling rate; and
- providing the reconstructed HS segment to a user or a process.

15. The method of claim 14, wherein the reconstructed HS segment includes one or more of an S1 segment, an S2 segment, an S3 segment, or an S4 segment within a cardiac cycle, and wherein reconstructing the HS segment includes reconstructing a first HS segment to have the second sampling rate, and reconstructing a second HS segment to have a third sampling rate different than the first and second sampling rates, the first and second HS segments representing different segments of a cardiac cycle.

16. The method of claim 14, wherein reconstructing the HS segment includes:
- producing reconstruction time windows each having a duration inversely proportional to the second sampling rate; and
- reconstructing the HS segment using a central tendency of HS data of the generated HS ensemble falling within the produced reconstruction time windows.

17. The method of claim 14, comprising:
- receiving one or more of physiologic parameters concurrently measured with the acceleration information, the one or more physiologic parameters including heart rates (HRs), cycle lengths (CLs), physical activity level, or respiratory rates; and
- generating the HS ensemble including portions of the received acceleration information over multiple cardiac cycles with corresponding received one or more physiologic parameters satisfying specified condition.

18. The method of claim 14, comprising generating the HS ensemble including portions of the received acceleration information over multiple cardiac cycles that are sensed during substantially the same time of a day.

19. The method of claim 14, comprising:
- sensing a body motion signal at the first sampling rate;
- detecting one or more of a physical activity level or a respiratory rate using the sensed body motion signal;
- identifying portions of the sensed body motion signal corresponding to the detected physical activity level falling within a specified physical activity range or the detected respiratory rate falling within a specified respiratory rate range; and
- generating the HS ensemble including multiple cardiac cycles of the identified portions of the sensed body motion signal.

20. The method of claim 14, comprising:
- generating a HS metric including an intensity metric or a timing metric of one or more of a first (S1), second (S2), third (S3), or fourth (S4) heart sound component measured from the reconstructed HS segment;
- detecting a cardiac event using the generated HS metric; and
- initiating or adjusting a therapy in response to the detected cardiac event.

* * * * *